US006271233B1

(12) United States Patent
Brazzell et al.

(10) Patent No.: US 6,271,233 B1
(45) Date of Patent: Aug. 7, 2001

(54) METHOD FOR TREATING OCULAR NEOVASCULAR DISEASES

(75) Inventors: Romulus Kimbro Brazzell, Alpharetta, GA (US); Jeanette Marjorie Wood, Biel Benken (CH); Peter Anthony Campochiaro, Baltimore, MD (US); Frances Elizabeth Kane, Gainesville, GA (US)

(73) Assignee: CIBA Vision Corporation, Deluth, GA (US)

( * ) Notice: Subject to any disclaimer, the term of this patent is extended or adjusted under 35 U.S.C. 154(b) by 0 days.

(21) Appl. No.: 09/371,746

(22) Filed: Aug. 10, 1999

(51) Int. Cl.[7] ..................................................... A01N 43/58
(52) U.S. Cl. ............................................ 514/249; 514/912
(58) Field of Search .................................. 514/248, 249, 514/912

(56) References Cited

FOREIGN PATENT DOCUMENTS

| 03106875 A2 | 5/1991 | (JP) . |
| WO 97/34876 | 9/1997 | (WO) . |
| WO 97/34920 | 9/1997 | (WO) . |
| WO 97/40831 | 11/1997 | (WO) . |
| WO 98/35958 | 8/1998 | (WO) . |

OTHER PUBLICATIONS

Chemical Abstracts, 69 : 19180. Parsons et al., 1965.*
European Patent Office Standard Search Report.
The 23rd German Cancer conference, Berlin 8–12 Jun. 1998, Germany Needs Interdisciplinary Approach to Cancer Research, International Cancer News, Jun. 8, 1998, pp. 1474–1475.
Protein Kinase C. Activation and Its Role in the Development of Vascular Compliclations in Diabetes Mellitus, Hidehiro Ishii, et al.
Pharmazeutische Zeitung, Christiane Berg vol. 34, 1998, pp. 1474–1475.
Proceedings of the American Association for Cancer Research, J. Wood, et al, Vo.. 39, Mar. 1998, pp. 96.

* cited by examiner

Primary Examiner—Zohreh Fay
(74) Attorney, Agent, or Firm—David E. Wildman (57) ABSTRACT

The invention relates to the use of certain phthalazines in the preparation of medicaments for the treatment of ocular neovascularization.

13 Claims, 8 Drawing Sheets

METHOD FOR TREATING OCULAR NEOVASCULAR DISEASES

The invention relates to new phthalazine derivatives for the manufacture of a pharmaceutical preparation for the treatment and prevention of ocular neovascular diseases. It further relates to the treatment and prevention of such ocular diseases the phthalazine derivatives.

BACKGROUND OF THE INVENTION

Two processes, the de novo formation of vessels from differentiating endothelial cells or angioblasts in the developing embryo (vasculogenesis) and the growth of new capillary vessels from existing blood vessels (angiogenesis), are involved in the development of the vascular systems of animal organs and tissues.

Recent findings show that at the centre of the network regulating the growth and differentiation of the vascular system and its components, both during embryonic development and normal growth and in a wide number of pathological anomalies and diseases, lies the angiogenic factor known as "Vascular Endothelial Growth Factor" (=VEGF), along with its cellular receptors. (see, Breier, et al., *Trends in Cell Biology* 6: 454–456, 1996).

VEGF receptors are transmembrane receptor tyrosine kinases. They are characterized by an extracellular domain with seven immunoglobulin-like domains and an intracellular tyrosine kinase domain. Various types of VEGF receptor are known, e.g. VEGFR-1, VEGFR-2, and VEGFR-3.

SUMMARY OF THE INVENTION

It has now been found that phthalazine derivatives of formula I, described below, have advantageous pharmacological properties and inhibit ocular neovascularization, including retinal neovascularization and choroidal neovascularization.

DETAILED DESCRIPTION OF THE INVENTION

The invention relates to the use of a compound of formula I, (1)

wherein
  n is 0 to 2,
  R is H or lower alkyl;
  X is imino, oxa, or thia;
  Y is aryl; and
  Z is unsubstituted or substituted pyridyl,
  or an N-oxide of the defined compound of formula I, wherein one or more N atoms carry an oxygen atom;
  in the manufacture of a composition for the treatment of ocular neovascular diseases, inlcuding retinal and choroidal neovascularization.

It further relates to a method of treating ocular neovascular diseases, and in particular choroidal and retinal neovascularization in an individual and in particular in humans, comprising administering a compound of formula I as defined above to said individual in need of such treatment.

As indicated above and below the addressed compounds are useful in the treatment of ischemic retinopathy, retinal neovascularization and choroidal neovascularization. Preference is given to the treatment of retinal neovascularization and choroidal neovascularization. More preferred is the treatment of retinal neovascularization. More preferred is also the treatment of choroidal neovascularization.

It has been found that the above compounds of formula I are typically 5–100 times more active than compounds of the prior art, which prior art compounds are associated with the inhibition of deregulated angiogenesis. In particular the present compounds are typically 10–50 times more active than compounds of the prior art. This measure relates independently either to efficacy and/or duration of action. Preference is given to efficacy.

The general terms used hereinbefore and hereinafter preferably have within the context of this disclosure the following meanings, unless otherwise indicated:

The prefix "lower" denotes a moiety having up to and including a maximum of 7, especially up to and including a maximum of 4 carbon atoms, the moieties in question being either linear or branched with single or multiple branching.

Where the plural form is used for compounds, salts, and the like, this is taken to mean also a single compound, salt, or the like.

Any asymmetric carbon atoms (for example in compounds of formula I [or an N-oxide thereof], wherein n=1 and R is lower alkyl) may be present in the (R)-, (S)- or (R,S)-configuration, preferably in the (R)- or (S)-configuration. Substituents at a double bond or a ring may be present in cis- (=Z—) or trans (=E—) form. The compounds may thus be present as mixtures of isomers or as pure isomers, preferably as enantiomer-pure diastereomers.

The index n is preferably 0 or 1, especially 0.

Lower alkyl is preferably $C_1$–$C_4$-alkyl, e.g. n-butyl, sec-butyl, tert-butyl, n-propyl, isopropyl, or more preferably methyl or ethyl.

In the preferred embodiment, aryl is an aromatic moiety having 6 to 14 carbon atoms, especially phenyl, naphthyl, fluorenyl or phenanthrenyl, the moieties defined above being unsubstituted or substituted by one or more, preferably up to three, especially one or two substituents, especially selected from amino, mono- or disubstituted amino, halogen, alkyl, substituted alkyl, hydroxy, etherified or esterified hydroxy, nitro, cyano, carboxy, esterified carboxy, alkanoyl, carbamoyl, N-mono- or N, N-disubstituted carbamoyl, amidino, guanidino, mercapto, sulfo, phenylthio, phenyl-lower alkylthio, alkylphenylthio, phenylsulfinyl, phenyl-lower alkylsulfinyl, alkylphenylsulfinyl, phenylsulfonyl, phenyl-lower alkylsulfonyl, and alkylphenylsulfonyl, or (as an alternative or in addition to the above group of substituents) selected from lower alkenyl, such as ethenyl, phenyl, lower alkylthio, such as methylthio, lower alkanoyl, such as acetyl, lower alkylmercapto, such as methylmercapto (—S—CH$_3$), halogen-lower alkylmercapto, such as trifluoromethylmercapto (—S—CF$_3$), lower alkylsulfonyl, halogen-lower alkylsulfonyl, such as especially trifluoromethane sulfonyl, dihydroxybora (—B(OH)$_2$), heterocyclyl, and lower alkylene dioxy bound at adjacent C-atoms of the ring, such as methylene dioxy; aryl is preferably phenyl which is either unsubstituted or independently substituted by one or two substituents selected from the group comprising amino; lower alkanoylamino, especially acetylamino; halogen, especially fluorine, chlorine, or bromine; lower alkyl, especially methyl or also ethyl or propyl; halogen-lower alkyl, especially trifluoromethyl; hydroxy; lower alkoxy, especially methoxy or also ethoxy; phenyl-lower alkoxy, especially benzyloxy; and cyano, or (as an alternative or in addition to the previous group of substituents) C$_8$–C$_{12}$alkoxy, especially n-decyloxy, carbamoyl, lower alkylcarbamoyl, such as n-methyl- or n-tert-butylcarbamoyl, lower alkanoyl, such as acetyl, phenyloxy, halogen-lower alkyloxy, such as trifluoromethoxy or 1,1,2,2-tetrafluoroethyloxy, lower alkoxycarbonyl, such as ethoxycarbonyl, lower alkylmercapto, such as methylmercapto, halogen-lower alkylmercapto, such as trifluoromethylmercapto, hydroxy-lower alkyl, such as hydroxymethyl or 1-hydroxymethyl, lower alkylsulfonyl, such as methane sulfonyl, halogen-lower alkylsulfonyl, such as trifluoromethane sulfonyl, phenylsulfonyl, dihydroxybora (—B(OH)$_2$), 2-methylpyrimidin-4-yl, oxazol-5-yl, 2-methyl-1,3-dioxolan-2-yl, 1H-pyrazol-3-yl, 1-methyl-pyrazol-3-yl and lower alkylene dioxy bound to two adjacent C-atoms, such as methylene dioxy.

Where mention is made hereinbefore and hereinafter to moieties or substituents as "an alternative or in addition to" the previous group of moieties or substituents, these moieties or substituents and those of the previous group are to be regarded together as one group of substituents from which the respective moieties may be selected, or especially as separate groups. The expression does not mean that one of the radicals following the expression may be added to a member of the previous group by binding. This applies, even if the expression "as an alternative or in addition to" is not mentioned again, for the moieties or substituents, as defined here, in the preferred compounds of formula I defined below.

Mono- or disubstituted amino is especially amino substituted by one or two moieties selected independently of one another from lower alkyl, such as methyl; hydroxy-lower alkyl, such as 2-hydroxyethyl; phenyl-lower alkyl; lower alkanoyl, such as acetyl; benzoyl; substituted benzoyl, wherein the phenyl moiety is unsubstituted or especially substituted by one or more, preferably one or two, substituents selected from nitro or amino, or also from halogen, amino, N-lower alkylamino, N,N-di-lower alkylamino, hydroxy, cyano, carboxy, lower alkoxycarbonyl, lower alkanoyl, and carbamoyl; and phenyl-lower alkoxycarbonyl, wherein the phenyl moiety is unsubstituted or especially substituted by one or more, preferably one or two, substituents selected from nitro or amino, or also from halogen, amino, N-lower alkylamino, N,N-di-lower alkylamino, hydroxy, cyano, carboxy, lower alkoxycarbonyl, lower alkanoyl, and carbamoyl; and is preferably N-lower alkylamino, such as N-methylamino, hydroxy-lower alkylamino, such as 2-hydroxyethylamino, phenyl-lower alkylamino, such as benzylamino, N,N-di-lower alkylamino, N-phenyl-lower alkyl-N-lower alkylamino, N,N-di-lower alkylphenylamino, lower alkanoylamino, such as acetylamino, or a substituent selected from the group comprising benzoylamino and phenyl-lower alkoxycarbonylamino, wherein the phenyl moiety in each case is unsubstituted or especially substituted by nitro or amino, or also by halogen, amino, N-lower alkylamino, N,N-di-lower alkylamino, hydroxy, cyano, carboxy, lower alkoxycarbonyl, lower alkanoyl or carbamoyl, or as an alternative or in addition to the previous group of moieties by aminocarbonylamino.

Halogen is preferably fluorine, chlorine, bromine, or iodine, more preferably fluorine, chlorine, or bromine.

In the preferred embodiment, alkyl has up to a maximum of 12 carbon atoms and is preferably lower alkyl, more preferably methyl, ethyl, n-propyl, isopropyl, or tert-butyl.

Substituted alkyl is alkyl as last defined, especially lower alkyl, preferably methyl; where one or more, especially up to three, substituents may be present, primarily from the group selected from halogen, especially fluorine, and also from amino, N-lower alkylamino, N,N-di-lower alkylamino, N-lower alkanoylamino, hydroxy, cyano, carboxy, lower alkoxycarbonyl, and phenyl-lower alkoxycarbonyl. Trifluoromethyl is especially preferred.

Etherified hydroxy is especially C$_8$–C$_{20}$alkyloxy, such as n-decyloxy, lower alkoxy, such as methoxy, ethoxy, isopropyloxy, or n-pentyloxy, phenyl-lower alkoxy, such as benzyloxy or phenyloxy, or as an alternative or in addition to the previous group C$_8$–C$_{20}$alkyloxy, such as n-decyloxy, halogen-lower alkoxy, such as trifluoromethyloxy or 1,1,2, 2-tetrafluoroethoxy.

Esterified hydroxy is especially lower alkanoyloxy, benzoyloxy, lower alkoxycarbonyloxy, such as tert-butoxycarbonyloxy, or phenyl-lower alkoxycarbonyloxy, such as benzyloxycarbonyloxy.

Esterified carboxy is especially lower alkoxycarbonyl, such as tert-butoxycarbonyl or ethoxycarbonyl, phenyl-lower alkoxycarbonyl, or phenyloxycarbonyl.

Alkanoyl is primarily alkylcarbonyl, especially lower alkanoyl, e.g. acetyl.

N-mono- or N,N-disubstituted carbamoyl is especially substituted by one or two substituents, lower alkyl, phenyl-lower alkyl, or hydroxy-lower alkyl, at the terminal nitrogen atom.

Alkylphenylthio is especially lower alkylphenylthio.

Alkylphenylsulfinyl is especially lower alkylphenylsulfinyl.

Alkylphenylsulfinyl is especially lower alkylphenylsulfinyl.

Unsubstituted pyridyl is preferably 3- or 4-pyridyl. Specially preferred is 4-pyridyl.

Substituted pyridyl is preferably 3- or 4-pyridyl which is substituted by one or two substituents, in particular selected from lower alkyl, preferably methyl, ethyl; halogen preferably chloro, fluoro, bromo; lower alkyl halides preferably trifluoromethyl; lower alkoxy preferably methoxy, ethoxy;

hydroxy; cyano; amino, N-lower alkylamino, N,N-di-lower alkylamino. Specially preferred is 4-pyridiyl substituted by methyl, chloro, fluoro, trifluoromethyl or methoxy.

Heterocyclyl is especially a five or six-membered heterocyclic system with 1 or 2 heteroatoms selected from the group comprising nitrogen, oxygen, and sulfur, which may be unsaturated or wholly or partly saturated, and is unsubstituted or substituted especially by lower alkyl, such as methyl; a moiety selected from 2-methylpyrimidin-4-yl, oxazol-5-yl, 2-methyl-1,3-dioxolan-2-yl, 1H-pyrazol-3-yl, and 1-methyl-pyrazol-3-yl is preferred.

Aryl in the form of phenyl which is substituted by lower alkylene dioxy bound to two adjacent C-atoms, such as methylenedioxy, is preferably 3,4-methylenedioxyphenyl.

An N-oxide of a compound of formula I is preferably an N-oxide in which a phthalazine-ring nitrogen or a nitrogen in the pyridin ring carries an oxygen atom, or several of the said nitrogen atoms carry an oxygen atom.

Salts are especially the pharmaceutically acceptable salts of compounds of formula I (or an N-oxide thereof).

When a basic group and an acid group are present in the same molecule, a compound of formula 1 (or an N-oxide thereof may also form internal salts.

In view of the close relationship between the novel compounds in free form and those in the form of their salts, including those salts that can be used as intermediates, for example in the purification or identification of the novel compounds, any reference to the free compounds hereinbefore and hereinafter is to be understood as referring also to the corresponding salts, as appropriate and expedient.

Background for Testing:

The retina is a tissue with very high metabolic activity that is oxygenated from the retinal and choroidal circulations, which each originate from branches of the ophthalmic artery. The choroidal circulation is derived from the long and short posterior ciliary arteries, which pierce the sclera and form successively smaller branches that supply the choriocapillaris, a vascular syncytium separated from the retina by the retinal pigmented epithelium (RPE). The photoreceptor layer of the retina has no blood vessels and receives oxygen by diffusion from the choriocapillaris. The retinal circulation is derived from the central retinal artery which enters the eye through the optic nerve, branches to form retinal arterioles that run along the surface of the retina, send penetrating branches throughout the inner two thirds of the retina, ending in the superficial and deep retinal capillary beds.

The retinal circulation develops first at the optic nerve and extends to the periphery of the retina, a process that occurs late in development, and in humans is completed shortly before term. In several species, including rats and mice, retinal vascular development is completed after birth. While it is not completely clear if this process represents physiologic angiogenesis, growth of blood vessels into avascular tissue, or vasculogenesis, development of blood vessels from pre-existent precursor cells, it clearly occurs along a spatial gradient from posterior to anterior. Hypoxia in the avascular peripheral retina results in upregulation of vascular endothelial growth factor (VEGF). (See, Alon, et al., Vascular Endothelial Growth Factors Acts as a Survival factor for Newly Formed Retinal Vessels and Has Implications for Retinopathy of Prematurity: *Nature Med.*, 1: 1024–1028, 1995). Hyperoxia inhibits development of retinal blood vessels, and in fact causes them to regress due to apoptosis of vascular endothelial cells. This regression is accompanied by downregulation of VEGF and is prevented by administration of exogenous VEGF. These data suggest that VEGF plays an important role in retinal vascular development.

Neonatal animals with hyperoxia-induced regression of retinal vessels that are put in room air, develop severe retinal hypoxia, dramatic upregulation of VEGF, and retinal neovascularization. (See, Pierce, et al., Vascular Endothelial Growth Factor/Vascular Permeability Factor for Expression in a Mouse Model of Retinal Neovascularization. *Proc Natl Acad Sci USA*, 92: 905–909, 1995.) This situation models that of retinopathy of prematurity (ROP) in humans, but also shares features with several disease processes in adults in which retinal vessels become damaged and occluded leading to retinal ischemia. These diseases are collectively referred to as ischemic retinopathies and include branch retinal vein occlusion and proliferative diabetic retinopathy, the most common cause of severe visual loss in people under 60 in developed countries. (See, Kahn, Blindness Caused by Diabetic Retinopathy, *Am J Ophthalmol*, 78: 58–67,1974.)

Much more is known about the cascade of events leading to retinal neovascularization than that for choroidal neovascularization. It is well established that retinal capillary nonperfusion leading to retinal hypoxia plays a central role (see, for example, Michaelson, The Mode of Development of the Vascular System of the Retina with some Observations on its Significance for Certain Retinal Diseases, *Trans Ophthalmol Soc UK*, 68: 137–180, 1948.) and that hypoxia results in the release of vascular endothelial growth factor (VEGF) which is the major stimulatory factor for retinal neovascularization (see, for example, Shweiki, et al., Vascular Endothelial Growth Factor Induced by Hypoxia May Mediate Hypoxia-initiated Angiogenesis, *Nature* 359: 843–845, 1992). It is uncertain whether hypoxia plays a role in the development of choroidal neovascularization. There is some suggestion that choroidal blood flow may be altered in patients with age-related macular degeneration (see, for example, Grunwald, et al., Foveolar Choroidal Blood Flow in Age-related Macular Degeneration, *Invest Ophthalmol Vis Sci* 39:385–390, 1998), but it is not clear if this is sufficient to cause hypoxia. Another possible source of hypoxia that has been suggested is diffuse thickening of Bruch's membrane with lipophilic material decreasing diffusion of oxygen from the choroid to the RPE and retina, but there are no data to support this hypothesis. Also, hypoxia is unlikely to be present in other disease processes associated with choroidal neovascularization that occur in young patients, such as ocular histoplasmosis. It is also uncertain whether VEGF is a major stimulatory factor for choroidal neovascularization. Increased levels of VEGF and FGF2 have been demonstrated in RPE cells in association with choroidal neovascularization (see, for example, Zhang, et al., Mitogenesis and Retinal Pigment Epithelial Cell Antigen Expression in the Rat After Krypton Laser Photocoagulation, *Invest Ophthalmol Vis Sci* 34:2412–2424, 1993), but there is no direct evidence that they are involved. In fact, it has recently demonstrated that the incidence of choroidal neovascularization in a murine model is not statistically different in FGF2 knockout mice compared to wild type mice, suggesting that FGF2 is not necessary for the occurrence of choroidal neovascularization. (See, Tobe, et al., Targeted Disruption of the FGF2 Gene Does Not Prevent Choroidal Neovascularization in a Murine Model, *Amer J Pathol* 1998, in press). Increased expression of VEGF in photoreceptors of transgenic mice results in neovascularization originating from retinal blood vessels, but not choroidal vessels. (See, Okamoto, et al., Transgenic Mice with Increased Expression of VEGF in the Retina: a New Model of Retinal Neovascularization, *Am J Pathol*, 151:281–291, 1997). Therefore, there are important differences between retinal and choroidal neovascularization. This suggests that pharmacologic treatments that show promise for retinal neovascularization can not be assumed to be efficacious for choroidal neovascularization and should be examined in appropriate animal models.

Two approaches that have shown some promise with regards to treatment of retinal neovascularization are antagonism of VEGF (see, for example, Aiello, et al., Suppression of Retinal Neovascularization in Vivo by Inhibition of Vascular Endothelial Growth Factor (VEGF) Using Soluble VEGF-receptor Chimeric Proteins, *Proc Natl Acad Sci USA* 92:10457–10461, 1995) and inhibition of protein kinase C (PKC) activity (see, Danis, et al., Inhibition of Intraocular Neovascularization Caused by Retinal Ischemia in Pigs by PKCbeta Inhibition with LY 333531. *Invest Ophthalmol Vis Sci*, 39:171–179,1998). Intravitreous injection of soluble VEGF receptor/IgG fusion proteins (see, *Proc Natl Acad Sci USA* 92:10457–10461, supra) or VEGF anti-sense oligonucleotides (see, Robinson, et al., Oligodeoxynucleotides Inhibit Retinal Neovascularization in a Murine Model of Proliferative Retinopathy. *Proc Natl Acad Sci USA*, 93:4851–4856,1996) each inhibited retinal neovascularization by about 50% in a murine model of oxygen-induced ischemic retinopathy. A specific antagonist of the PKCβ isoforms partially inhibited retinal neovascularization after laser-induced branch vein occlusion in pigs (see, *Invest Ophthalmol Vis Sci*, 39:171–179, supra). The preliminary data in this application indicates that GCP 79787D provides a major advance in the treatment of both retinal and choroidal neovascularization.

Drug Treatment of Mice with Ischemic Retinopathy

Ischemic retinopathy is produced in C57/BL6J mice by a method described by Smith et al. (See, Smith, et al., Oxygen-induced Retinopathy in the Mouse, *Invest Ophthalmol Vis Sci*, 35:101–111, 1994). Seven-day-old mice and their mothers are placed in an airtight incubator and exposed to an atmosphere of 75±3% oxygen for 5 days. Incubator temperature is maintained at 23±2° C., and oxygen is measured every 8 hours with an oxygen analyzer. After 5 days, the mice are removed from the incubator, placed in room air, and drug treatment is begun. Drugs are diluted in phosphate-buffered saline (PBS) or 1% dimethyl sulfoxide depending upon their solubility characteristics and then diluted to their final concentration with PBS. Vehicle (control) or vehicle containing various concentrations of drug (volume =50 μl in neonates and 100 μl in adult mice) is placed in the stomach by gavage. After 5 days of treatment at P17, mice are sacrificed, eyes are rapidly removed and frozen in optimum cutting temperature embedding compound (OCT; Miles Diagnostics, Elkhart, Ind.) or fixed in 10% phosphate-buffered formalin and embedded in paraffin. Adult C57BL6J mice are also treated by gavage with drug or vehicle and after 5 days, they are sacrificed and their eyes are processed for frozen or paraffin sections.

Quantitation of Retinal Neovascularization

Frozen sections (10 μm) of eyes from drug-treated and control mice are histochemically stained with biotinylated griffonia simplicifolia lectin B4 (Vector Laboratories, Burlingame, Calif.) which selectively binds to endothelial cells. Slides are incubated in methanol/$H_2O_2$ for 30 minutes at 4° C., washed with 0.05 M Tris-buffered saline, pH 7.6 (TBS), and incubated for 30 minutes in 10% normal porcine serum. Slides are rinsed with 0.05M TBS and incubated 2 hours at room temperature with biotinylated lectin. After being rinsed with 0.05M TBS, slides are incubated with avidin coupled to peroxidase (Vector Laboratories) for 45 minutes at room temperature. After being washed for 10 minutes with 0.05 M TBS, slides are incubated with diaminobenzidine to give a brown reaction product. Some slides are counterstained with hematoxyln and all are mounted with Cytoseal.

To perform quantitative assessments, 10 μm serial sections are cut through the entire extent of each eye. The entire eye is sampled by staining sections roughly 50–60 μm apart, which provided 13 sections per eye for analysis. Lectin-stained sections are examined with an Axioskop microscope (Zeiss, Thornwood, N.Y.) and images are digitized using a 3 CCD color video camera (IK-TU40A, Toshiba, Tokyo, Japan) and a frame grabber. Image-Pro Plus software (Media Cybernetics, Silver Spring, Md.) is used to delineate lectin-stained cells on the surface of the retina and their area is measured. The mean of the 13 measurements from each eye is used as a single experimental value.

Drug Treatment of Mice During Retinal Vascular Development

Litters of newborn C57/BL6J mice are divided into treatment and control groups which received daily subcutaneous injections of 10 mg/kg of drug or vehicle, respectively. At P7 or P10, mice are anesthetized with ether, and perfused with 1 ml of phosphate-buffered saline containing 50 mg/ml of fluorescein-labeled dextran ($2 \times 10^6$ average mw, Sigma, St. Louis, Mo.) as previously described (See, Tobe, et al., Evolution of Neovascularization in Mice with Overexpression of VEGF in Photoreceptors, *Invest Ophthalmol Vis Sci*, 39:180–188, 1998). The eyes are removed and fixed for 1 hour in 10% phosphate-buffered formalin. The cornea and lens are removed and the entire retina is carefully dissected from the eyecup, radially cut from the edge of the retina to the equator in all 4 quadrants, and flat-mounted in Aquamount with photoreceptors facing upward. Flat-mounts are examined by fluorescence microscopy and images are digitized using a 3 CCD color video camera (IK-TU40A, Toshiba, Tokyo, Japan) and a frame grabber. Image-Pro Plus software (Media Cybernetics, Silver Spring, Md.) is used to measure the distance from the center of the optic nerve to the leading front of developing retinal vessels in each quadrant and the mean is used as a single experimental value.

Drug Treatment of Mice with Choroidal Neovascularization

Choroidal neovascularization is generated by modification of a previously described technique. (Tobe, et al., Targeted Disruption of the FGF2 Gene Does Not Prevent Choroidal Neovascularization in a Murine Model. *Amer J Pathol* 1998, in press) Briefly, 4 to 5 week old male C57BU6J mice are anesthetized with ketamine hydrochloride (100 mg/kg body weight) and the pupils are dilated with 1% tropicamide. Three burns of krypton laser photocoagulation (100pm spot size, 0.1 seconds duration, 150 mW) are delivered to each retina using the slit lamp delivery system of a Coherent Model 920 Photocoagulator and a hand held cover slide as a contact lens. Burns are performed in the 9, 12, and 3 o'clock positions of the posterior pole of the retina. Production of a bubble at the time of laser, which indicates rupture of Bruch's membrane, is an important factor in obtaining CNV [16], so only mice in which a bubble is produced for all three burns are included in the study. Ten mice are randomly assigned to treatment with vehicle alone and 10 mice received vehicle containing 120 μmoles/kg/day of one of the test drugs given orally by gavage. After 14 days, the mice are killed with an overdose of pentobarbital sodium, and their eyes are rapidly removed and frozen in optimal cutting temperature embedding compound (OCT).

Quantitation of Choroidal Neovascularization

Frozen serial sections (10 μm) are cut through the entire extent of each burn and histochemically stained with biotinylated griffonia simplicifolia lectin B4 (Vector

Laboratories, Burlingame, Calif.), which selectively binds to endothelial cells. Slides are incubated in methanol/$H_2O_2$ for 30 minutes at 4° C., washed with 0.05 M TBS, and incubated for 30 minutes in 10% normal swine serum. Slides are rinsed with 0.05M TBS and incubated 2 hours at 37° C. with biotinylated lectin. After being rinsed with 0.05M TBS, slides are incubated with Streptavidin-phosphatase (Kirkegaard and Perry Laboratories, Cabin John, Md.) for 30 minutes at room temperature. After a 10 minute wash in 0.05 M Tris buffer, pH 7.6, slides are developed in Histomark Red (Kirkegaard and Perry) to give a red reaction product, and mounted with Cytoseal (Stephens Scientific, Riverdale, N.J.). Some slides are counterstained with Contrast Blue (Kirkegaard and Perry).

To perform quantitative assessments, lectin-stained sections are examined with an Axioskop microscope (Zeiss, Thornwood, N.Y.) and images are digitized using a 3 CCD color video camera (IK-TU40A, Toshiba, Tokyo, Japan) and a frame grabber. Image-Pro Plus software (Media Cybernetics, Silver Spring, Md.) is used to delineate and measure the area of lectin-stained blood vessels in the subretinal space. For each lesion, area measurements are made for all sections on which some of the lesion appeared and added together to give the integrated area measurement. Values are averaged to give one experimental value per mouse. A 2-sample t-test for unequal variances is performed to compare the log mean integrated area between treatment and control mice.

Definition of Chemical Structures (CGP 79787D, CGP 57 148B and CGP 53 716)

CGP 79787D

CGP 53'716

CGP 57'148

Identification of Relatively Selective Tyrosine Kinase Inhibitors

Table 1 shows the ability of various drugs to inhibit the phosphorylation of poly(GluTyr) by GST-fusion proteins of the kinase domains of several tyrosine kinase receptors using a standard tyrosine kinase assay. CGP 79787D is a good inhibitor of phosphorylation by the kinase domains of human VEGF receptors 1 and 2, and PDGF receptor; it is about 10-fold less potent as an inhibitor of mouse VEGF receptor 2 compared to the human receptor, but still inhibits at a reasonable concentration ($IC_{50}$=290 nM). CGP 79787D is a poor inhibitor of phosphorylation by the kinase domain of all other tyrosine kinase and serine/threonine kinases tested (IC50>1 $\mu$M, Table 1). CGP 57 148B and CGP 53 716 are potent inhibitors of phosphorylation by the kinase domain of PDGF receptor, BCR ABL, and v-ABL, and provide little or no inhibitory activity of other RTKs including VEGF receptors.

TABLE 1

| | Kinase Inhibitory Profiles $I^{C}50$ ($\mu$M) | | |
|---|---|---|---|
| Tyrosine Kinase | GCP 79787D | GCP 53716 | CGP 57148 |
| KDR | 0.13 | >1 | — |
| Flt-1 | 0.34 | >1 | — |
| Flk-1 | 0.49 | >1 | — |
| PDGF-R$\beta$ | 0.2 | 6 | .83 |
| c-Kit | 0.413 | — | — |
| FGF-1 | >50 | — | — |
| Tie-2 | >1 | >1 | — |
| C-Met | >1 | >10 | — |
| EGF-R | 34 | >100 | >100 |
| C-Scr | >10 | >100 | >100 |
| V-Abl | >10 | 0.4 | 0.038 |

In vivo activity requires drugs to enter cells and therefore agents are tested in cellular autophosphorylation assays, using Chinese hamster ovary cells transfected with one of several RTK genes. CGP 79787D inhibits autophosphorylation of VEGF receptors, PDGF receptors, and c-Kit, but is a poor inhibitor of c-erbB2 or insulin receptor. CGP 57 148B and CGP 53 716 are potent inhibitors of PDGF receptors, but are poor inhibitors of other receptors tested including VEGF receptors. Therefore, CGP 79787D inhibits the tyrosine kinase activity of growth factor receptors belonging to the same family (class III), while CGP 57 148B and CGP 53 716 are more selective and only block PDGF receptors.

Figure 1A:
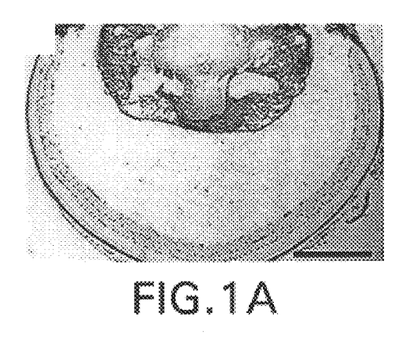
FIG. 1 illustrates blood vessels in retinas of treated and untreated mice.
Figure 1B:
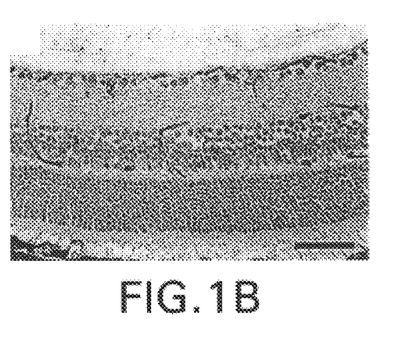
Figure 1C:
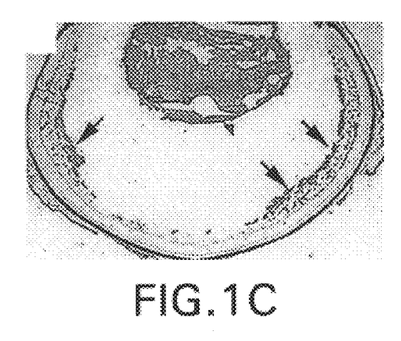
Figure 1D:
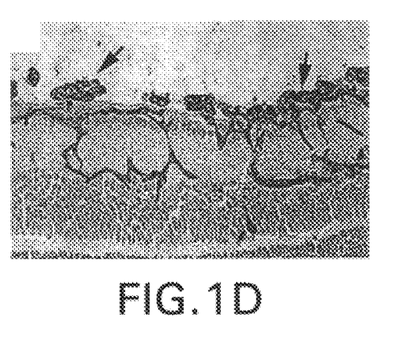
Figure 1E:
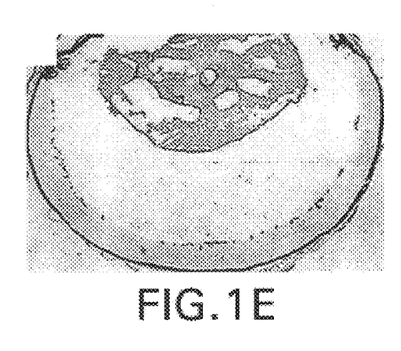
Figure 1F:
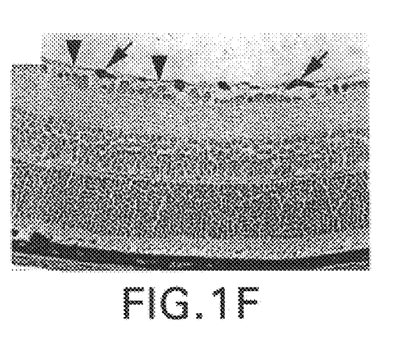
Figure 1G:
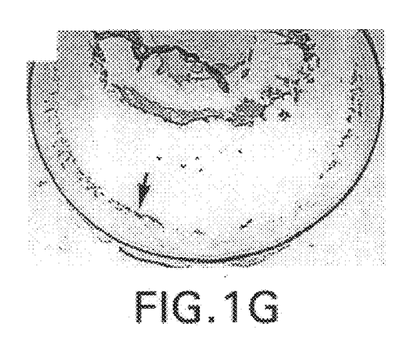
Figure 1H:
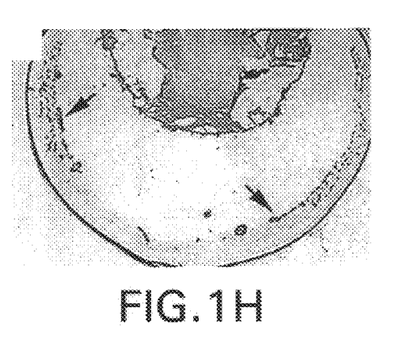
Figure 2:
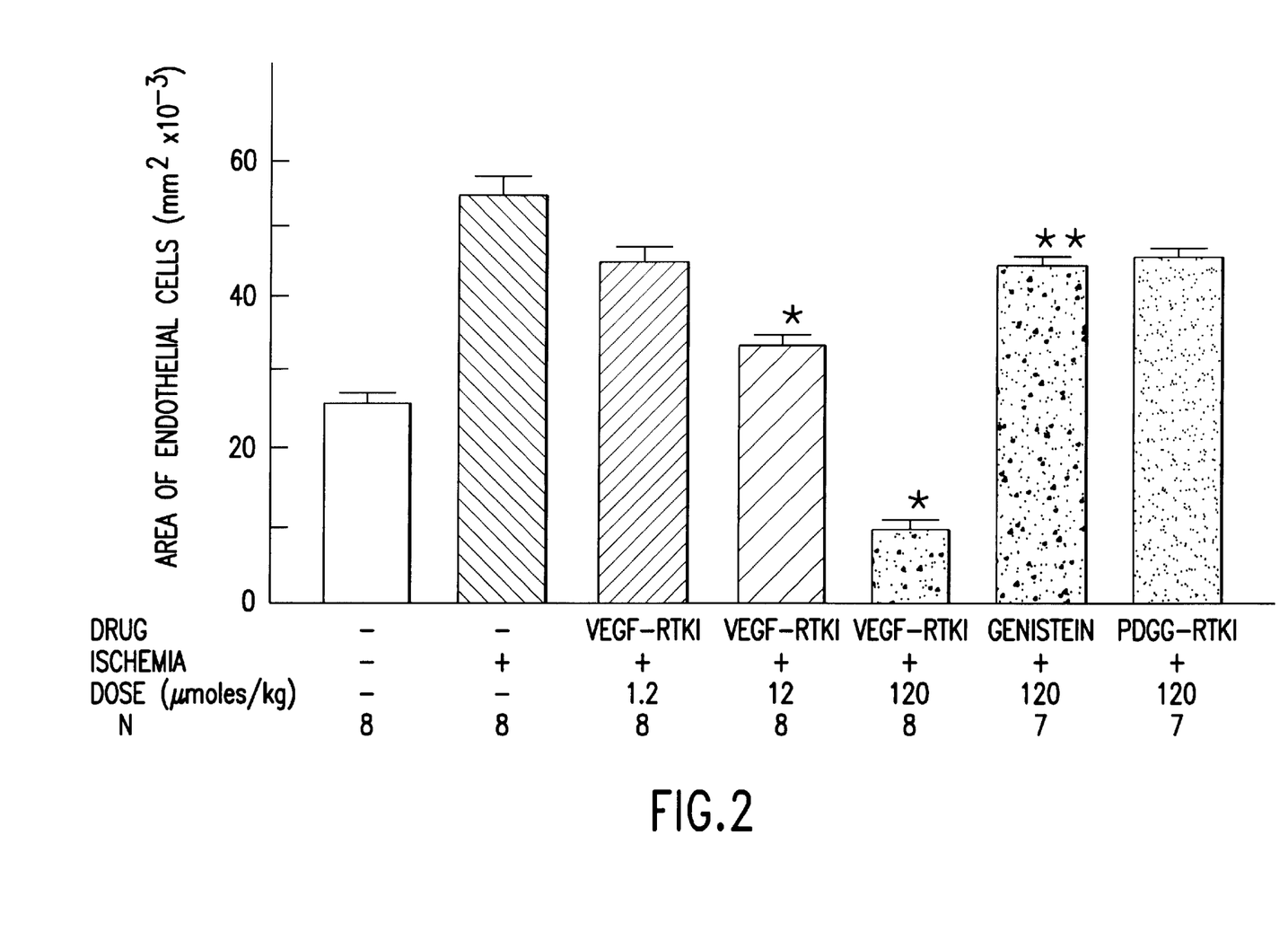
FIG. 2 illustrates the areas of endothelial cell staining for treated and untreated mice cells.
Figure 3A:
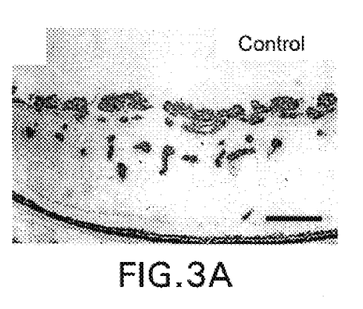
FIG. 3 illustrates endothelial staining in the retina of mice.
Figure 3B:
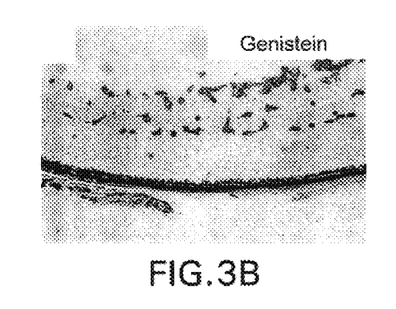
Figure 3C:
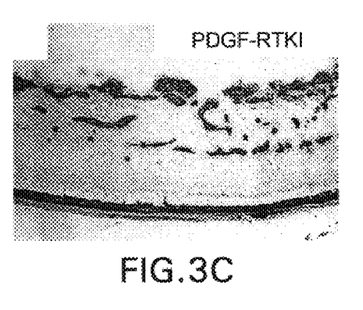
Figure 3D:
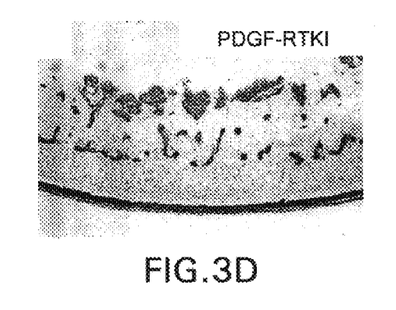

CGP 79787D Inhibits Retinal Neovascularization in Mice with Ischemic Retinopathy Griffonia simplicifolia lectin-stained retinas of nonischemic P17 mice show normal vessels in the superficial and deep capillary beds with a few connecting vessels (FIG. 1A and 1B). P17 mice with ischemic retinopathy show a marked increase in the area of endothelial cell staining throughout the retina with large clumps of cells on the retinal surface (FIGS. 1C, 1D, and 2, column 2), not seen in nonischemic retinas. P17 mice with ischemic retinopathy treated with 25 mg/kg twice a day of CGP 79787D have a dramatic decrease in endothelial cell staining within the retina (FIGS. 1E &F) that is significantly less than vehicle-treated mice, and also less than nonischemic P17 mice (FIG. 2, columns 1,2, and 5). High magnification shows that there are no identifiable endothelial cells on the surface of the retina, indicating that there is complete inhibition of neovascularization (FIG. 1F). There is also a striking absence of endothelial cell staining in the inner nuclear layer and outer plexiform layer where the deep capillary bed is normally located. P17 mice with ischemic retinopathy treated with 2.5 mg/kg twice a day of CGP 79787D show decreased endothelial cell staining in the retina that is significantly less than vehicle-treated controls (FIGS. 1G and 2, columns 2 and 4). There is also some decrease in endothelial staining in the inner nuclear layer. P17 mice with ischemic retinopathy treated with 0.25 mg/kg show decreased total endothelial staining in the retina that is not statistically significant, and there is no identifiable decrease in staining in the inner nuclear layer (FIGS. 1H and 2, columns 2 and 3). At doses comparable to the highest dose of CGP 79787D used, the 2 selective PDGF RTK inhibitors, CGP 57 148B and CGP 53 716, cause no significant decrease in endothelial staining in the retina of mice with ischemic retinopathy (FIGS. 2, columns 2 and 6, FIGS. 3C & D). Genistein (4',5,7-trihydroxyisoflavone) is a relatively weak, nonspecific inhibitor of RTKs. At a dose comparable to the highest dose of CGP 79787D, it causes no significant decrease in endothelial staining in the retina of mice with ischemic retinopathy (FIG. 2, columns 2 and 7 and FIG. 3B).

CGP 79787D Inhibits Retinal Vascular Development

Figure 4A:
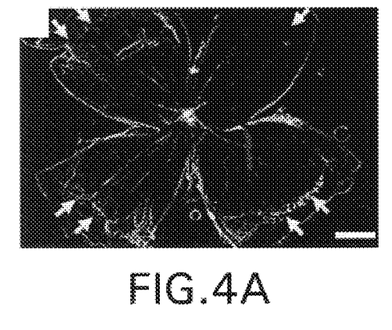
FIGS. 4 and 5 illustrate inhibition of retinal vascular development by a phathalazine derivative.
Figure 4B:
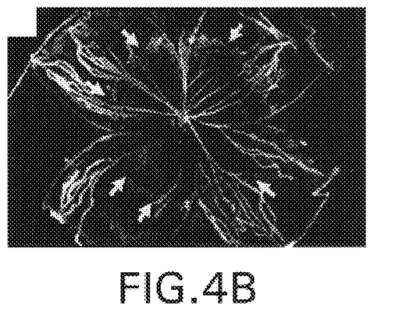
Figure 4C:
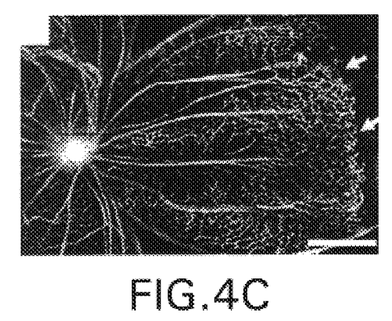
Figure 4D:
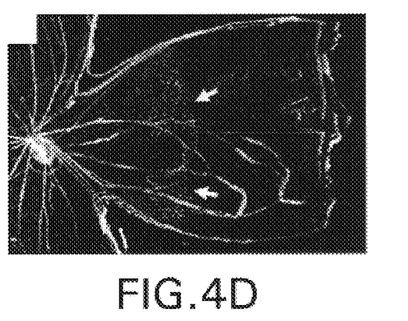
Figure 4E:
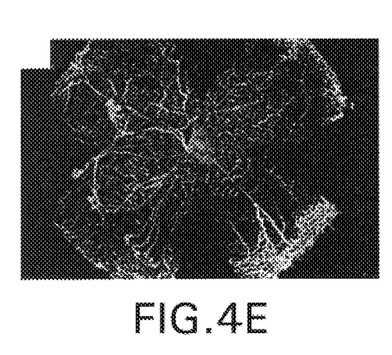
Figure 4F:
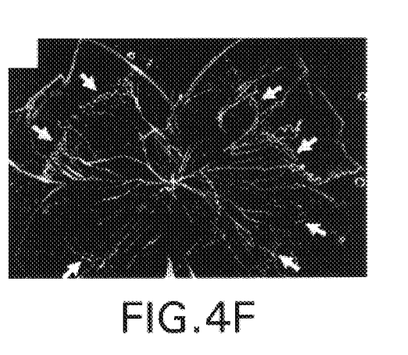
Figure 4G:
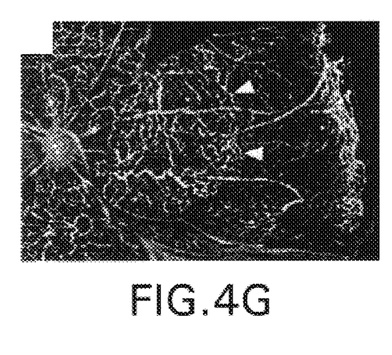
Figure 4H:
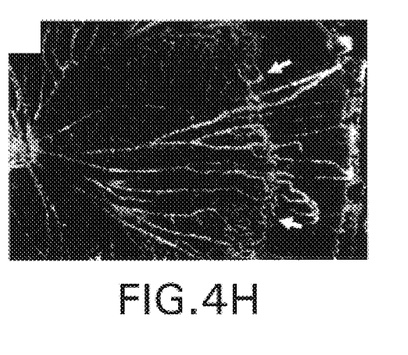
Figure 5:
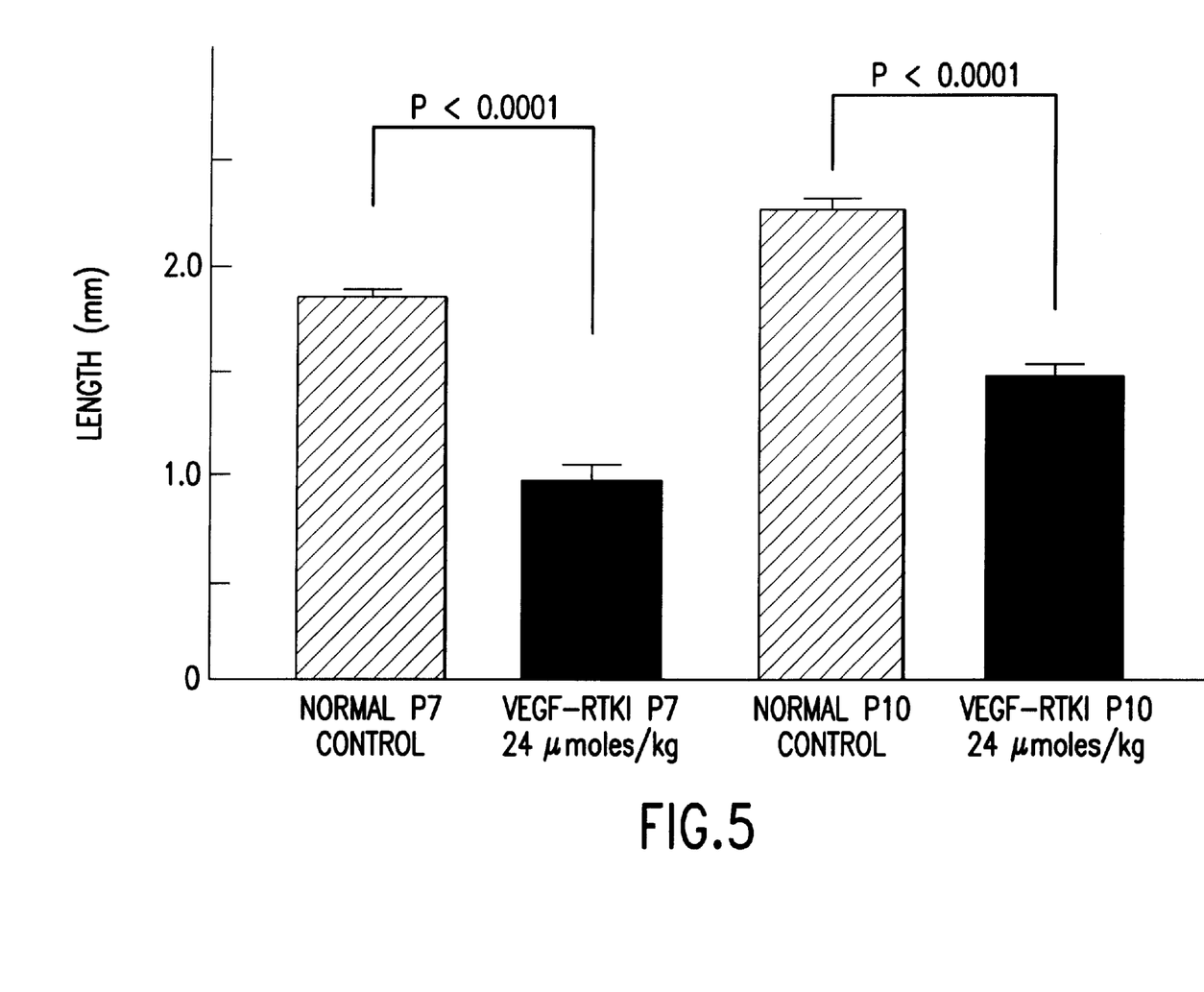

Neonatal mice are treated with injections of 10 mg/kg of CGP 79787D or vehicle alone starting on P0, and on P7 or P10 they are perfused with fluorescein-labeled dextran and retinal whole mounts are prepared. At P7, retinal vessels in vehicle-treated mice have almost reached the peripheral edge of retina, but in CGP 79787D-treated mice they have only extended about half way to the periphery (FIGS. 4A and B). At P10, the superficial capillary bed is complete and extends all the way to the peripheral edge of the retina, and the deep capillary bed is partially developed. But in CGP 79787D-treated mice, the superficial capillary bed has not yet reached the edge of the retina (FIGS. 4C and D). These differences are highly significant (FIG. 5) and demonstrate that CGP 79787D inhibits retinal vascular development as well as pathologic retinal neovascularization.

CGP 79787D has no Identifiable Effect on Retinal Vessels in Adult Mice

Figure 6A:
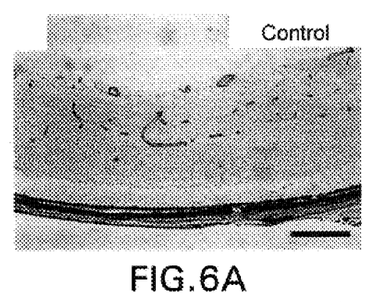
FIGS. 6 and 7 illustrate non-toxicity of a phathalazine derivative.
Figure 6B:
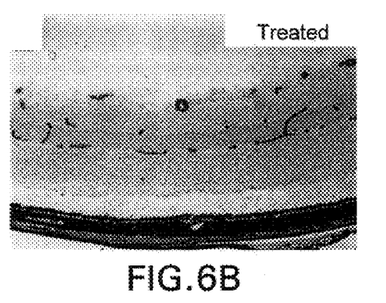
Figure 6C:
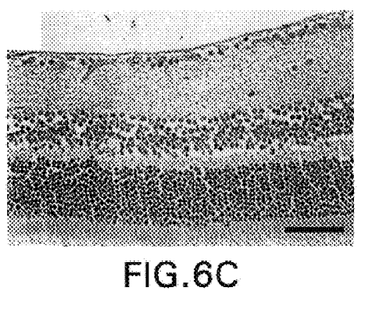
Figure 6D:
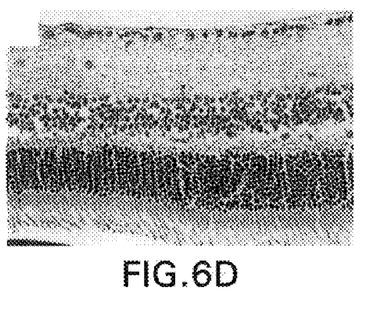
Figure 7:
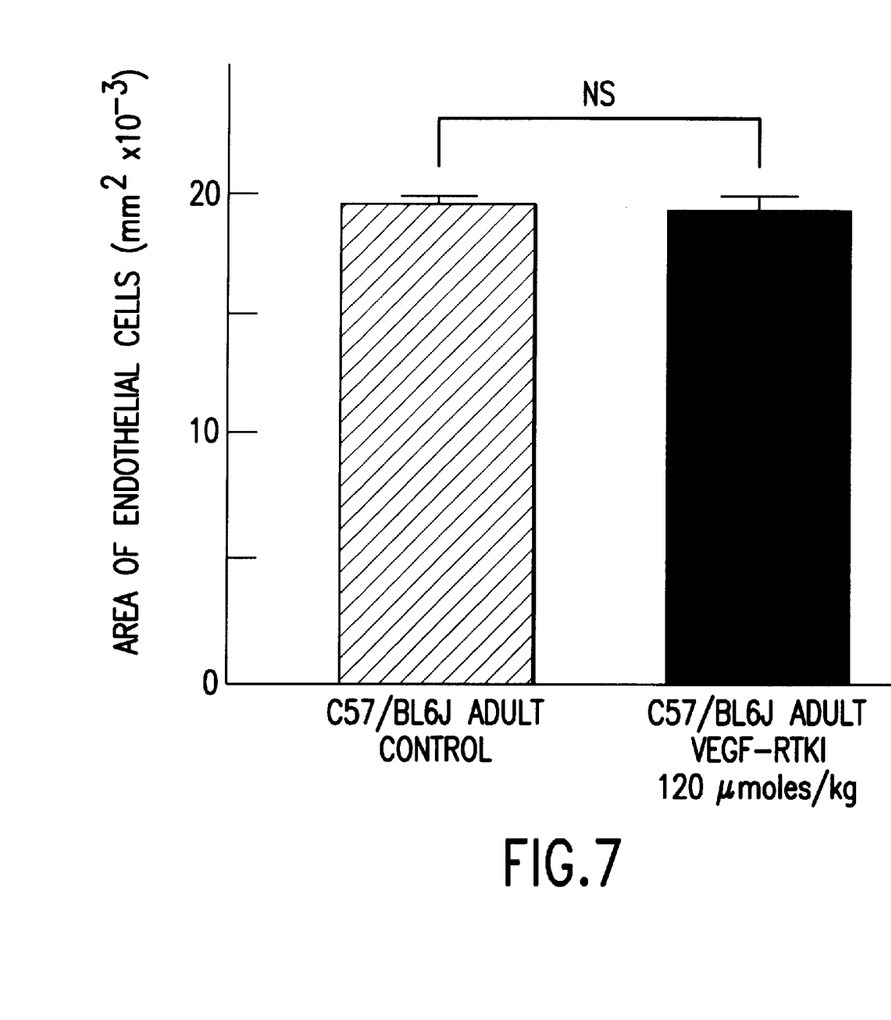

Adult mice are treated with 50 mg/kg/day of CGP 79787D, a dose that completely inhibits retinal neovascularization in oxygen-induced ischemic retinopathy and also inhibits development of the deep capillary bed. There is no difference in the total area of endothelial staining in the retina or the appearance of retinal vessels in CGP 79787D-treated mice (FIG. 6A & C) compared to vehicle-treated mice (FIG. 6B & D and FIG. 7). This suggests that CGP 79787D is not toxic to endothelial cells of mature vessels.

CGP 79787D Inhibits Choroidal Neovascularization

Figure 8A:
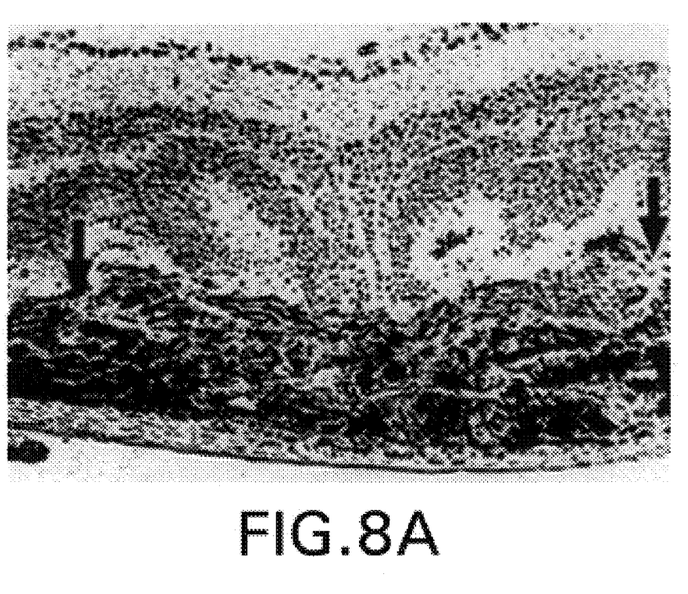
FIG. 8 illustrates inhibition of chorodial neovacularization by a phathalazine derivative.
Figure 8B:
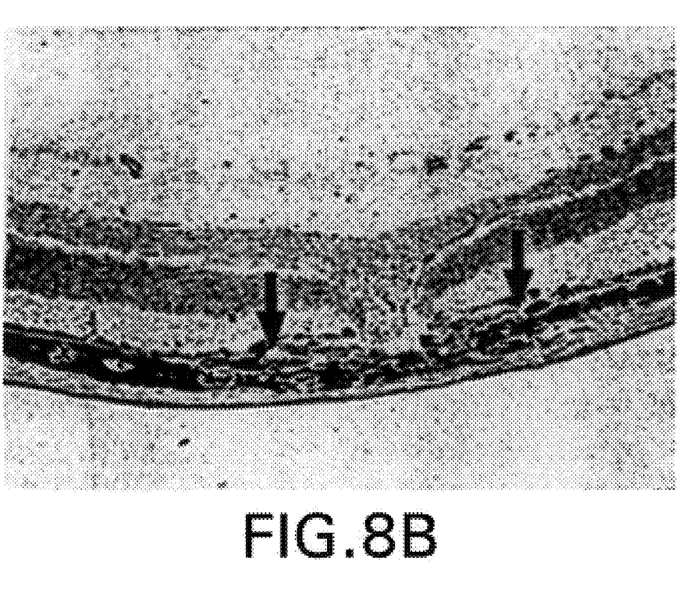

Two weeks after laser, all lesions in both groups of mice showed a discontinuity in Bruch's membrane with roughly equivalent damage to the overlying retina. All mice treated with vehicle alone showed large areas of choroidal neovascularization at the site of each laser-induced rupture of Bruch's membrane (FIG. 8A). There was proliferation of RPE cells along the margin of the new vessels. Retinal blood vessels stained with lectin were seen in the overlying retina. In contrast, all mice given 50 mg/kg/day of CGP 79787D by gavage had very little if any choroidal neovascularization at the site of each laser-induced rupture of Bruch's membrane (FIG. 8B). In most instances, there was no identifiable lectin-stained neovascular tissue throughout the entire burn, but some burns contained regions in which there were thin discs of lectin-stained tissue. There was mild proliferation of RPE cells. Despite the marked decrease in choroidal neovascularization in the eyes of treated mice, the overlying retinal vessels appeared normal. This is best seen in sections with no counterstain.

Quantitation of the integrated area of lectin staining per lesion showed a dramatic decrease in mice treated with CGP 79787D ($0.011243 \pm 0.0014829$ mm$^2$) compared to lesions in mice treated with vehicle alone ($0.0713812 \pm 0.0066723$ mm$^2$). This difference was highly statistically significant ($p=0.005$; $n=5$).

The above data demonstrate that it is possible to achieve complete inhibition of retinal neovascularization by oral treatment with CGP 79787D in the murine model of oxygen induced ischemic retinopathy. Based on the tyrosine kinase selectivity data, it is anticipated that the compound will be at least as effective in mammals, especially in humans, as mice.

The above data demonstrate that blockade of VEGF signaling does not damage mature retinal or choroidal blood vessels.

The above data demonstrate too that blockade of VEGF signaling inhibits retinal vascular development.

The above data demonstrate that blockade of VEGF signaling inhibits choroidal neovascularization.

CGP 79787D is useful for treatment and prevention of proliferative diabetic retinopathy and other causes of retinal neovascularization in adults. This is a large group of patients, because diabetic retinopathy is the most common cause of blindness in young patients of developed nations. CGP 79787D is also useful for treatment and prevention of choroidal neovascularization due to age-related exudative macular degeneration and other diseases. This is a very large group of patients because age-related macular degeneration is the most common cause of legal blindness in Americans over 60 years of age. CGP 79787D is useful in the treatment and prevention of ocular neovascular diseases.

Preferred Compounds

With the groups of preferred compounds of formula I mentioned hereinafter, definitions of substituents from the general definitions mentioned hereinbefore may reasonably be used, for example, to replace more general definitions with more specific definitions or especially with definitions characterized as being preferred.

Preference is given to a compound of formula I wherein n is 0 or 1,

R is H or lower alkyl, especially H or methyl,

X is imino, oxa, or thia,

Y is phenyl, which is unsubstituted or is substituted by one or two substituents independently of one another from the group comprising amino; lower alkanoylamino, especially acetylamino; halogen, especially fluorine, chlorine, or bromine; lower alkyl, especially methyl or also ethyl or propyl; halogen-lower alkyl, especially trifluoromethyl; hydroxy; lower alkoxy, especially methoxy or also ethoxy; phenyl-lower alkoxy, especially benzyloxy; and cyano, or (as an alternative or in addition to the previous group of substituents) lower alkenyl, such as ethenyl, $C_8$–$C_{12}$alkoxy, especially n-decyloxy, lower alkoxycarbonyl, such as tert-butoxycarbonyl, carbamoyl, lower alkylcarbamoyl, such as N-methyl- or N-tert-butylcarbamoyl, lower alkanoyl, such as acetyl, phenyloxy, halogen-lower alkyloxy, such as trifluoromethoxy or 1,1,2,2-tetrafluoroethyloxy, lower alkoxycarbonyl, such as ethoxycarbonyl, lower alkylmercapto, such as methylmercapto, halogen-lower alkylmercapto, such as trifluoromethylmercapto, hydroxy-lower alkyl, such as hydroxymethyl oder 1-hydroxymethyl, lower alkylsulfonyl, such as methanesulfonyl, halogen-lower alkylsulfonyl, such as trifluoromethanesulfonyl, phenylsulfonyl, dihydroxybora (—B(OH)$_2$), 2-methylpyrimidin-4-yl, oxazol-5-yl, 2-methyl-1,3-dioxolan-2-yl, 1h-pyrazol-3-yl, 1-methyl-pyrazol-3-yl and lower alkylenedioxy bound to two adjacent C-atoms, such as methylenedioxy, or is also pyridyl, especially 3-pyridyl; especially phenyl, 2-, 3- or 4-aminophenyl, 2-, 3- or 4-acetylaminophenyl, 2-, 3- or 4-fluorophenyl, 2-, 3- or 4-chlorophenyl, 2-, 3- or 4-bromophenyl, 2,3-, 2,4-, 2,5- or 3,4-dichlorophenyl, chlorofluorophenyl, such as 3-chloro-4-fluorophenyl or also 4-chloro-2-fluoroanilino, 2-, 3- or 4-methylphenyl, 2-, 3- or 4-ethylphenyl, 2-, 3-propylphenyl, methylfluorophenyl, such as 3-fluoro-4-methylphenyl, 2-, 3- or 4-trifluoromethylphenyl, 2-, 3- or 4-hydroxyphenyl, 2-, 3- or 4-methoxyphenyl, 2-, 3- or 4-ethoxyphenyl, methoxychlorophenyl, such as 3-chloro-4-methoxycarbonyl, 2-, 3- or 4-benzyloxyphenyl, 2-, 3- or 4-cyanophenyl, or also 2-, 3- or 4-pyridyl; and Z is 3- or 4-pyridyl, which is unsubstituted or is substituted by one or two substituents independently of one another from the group comprising halogen, especially fluorine, chlorine, or bromine; lower alkyl, especially methyl or also ethyl or propyl; halogen-lower alkyl, especially trifluoromethyl; hydroxy; lower alkoxy, especially methoxy or also ethoxy.

Special preference is given to a compound of formula I, n is 0 or 1,

R is H,

X is imino,

Y is phenyl, which is unsubstituted or is substituted by one or two substituents independently of one another from the group comprising amino; lower alkanoylamino, especially acetylamino; halogen, especially fluorine, chlorine, or bromine; lower alkyl, especially methyl; halogen-lower alkyl, especially trifluoromethyl; hydroxy; lower alkoxy, especially methoxy; phenyl-lower alkoxy, especially benzyloxy; and cyano; especially phenyl, 2-, 3- or 4-aminophenyl, 2-, 3- or 4-acetylaminophenyl, 2-, 3- or 4-fluorophenyl, 2-, 3- or 4-chlorophenyl, 2-, 3- or 4-bromophenyl, 2,3-, 2,4-, 2,5- or 3,4-dichlorophenyl, chlorofluorophenyl, such as 3-chloro-4-fluorophenyl, 2,- 3- or 4-methylphenyl, 2-, 3- or 4-trifluoromethylphenyl, 2-, 3- or 4-hydroxyphenyl, 2-, 3- or 4-methoxycarbonyl, methoxychlorophenyl, such as 3-chloro-4-methoxycarbonyl, 2-, 3- or 4-benzyloxyphenyl, or 2-, 3- or 4-cyanophenyl; and Z is 4-pyridyl, which is unsubstituted or is substituted by a substituent from the group consisting of halogen, especially fluorine, chlorine, or bromine; lower alkyl, especially methyl or also ethyl or propyl; halogen-lower alkyl, especially trifluoromethyl; hydroxy; lower alkoxy, especially methoxy.

Special preference is also given to a compound of formula I, n is 0 or 1,

R is H,

X is imino,

Y is phenyl, which is unsubstituted or is substituted by one or two substituents independently of one another from the group comprising halogen, especially fluorine, chlorine, or bromine; lower alkyl, especially methyl; halogen-lower alkyl, especially trifluoromethyl; hydroxy; lower alkoxy, especially methoxy; cyano; and Z is 4-pyridyl, which is unsubstituted or is substituted by a substituent from the group consisting of halogen, especially fluorine, or chlorine; lower alkyl, especially methyl; halogen-lower alkyl, especially trifluoromethyl; hydroxy; lower alkoxy, especially methoxy.

Special preference is also given to a compound of formula I, n is 0,

X is imino,

Y is phenyl, which is unsubstituted or is substituted by one substituent selected from the group consisting of fluorine, chlorine; methyl; trifluoromethyl; hydroxy; cyano and methoxy; and Z is 4-pyridyl, which is unsubstituted or is substituted by a substituent selected from the group consisting of fluorine, or chlorine; methyl; trifluoromethyl; hydroxy; methoxy.

Special preference is also given to a compound of formula I, n is 0,

X is imino,

Y is phenyl, which is unsubstituted or is substituted by one substituent selected from the group consisting of fluorine, chlorine; methyl; methoxy; cyano and trifluoromethyl; and Z is 4-pyridyl, which is unsubstituted or is substituted by a substituent selected from the group consisting of fluorine, or chlorine; and methyl.

High preference is given to a compound selected from the group consisting of:

1-(4-Chloroanilino)-4-(4-pyridylmethyl)phthalazine;

1-(3-Chloroanilino)-4-(4-pyridylmethyl)phthalazine;

1-Anilino-4-(4-pyridylmethyl)phthalazine;

1-Benzylamino-4-(4-pyridylmethyl)phthalazine;

1-(4-Methoxyanilino)-4-(4-pyridylmethyl)phthalazine;

1-(3-Benzyloxyanilino)-4-(4-pyridylmethyl)phthalazine;

1-(3-Methoxyanilino)-4-(4-pyridylmethyl)phthalazine;

1-(2-Methoxyanilino)-4-(4-pyridylmethyl)phthalazine;

1-(4-Trifluoromethylanilino)-4-(4-pyridylmethyl) phthalazine;

1-(4-Fluoroanilino)-4-(4-pyridylmethyl)phthalazine;

1-(3-Hydroxyanilino)-4-(4-pyridylmethyl)phthalazine;

1-(4-Hydroxyanilino)-4-(4-pyridylmethyl)phthalazine;

1-(3-Aminoanilino)-4-(4-pyridylmethyl)phthalazine;

1-(3,4-Dichloroanilino)-4-(4-pyridylmethyl)phthalazine;

1-(4-Bromoanilino)-4-(4-pyridylmethyl)phthalazine;

1-(3-Chloro-4-methoxyanilino)-4-(4-pyridylmethyl) phthalazine;

1-(4-Cyanoanilino)-4-(4-pyridylmethyl)phthalazine;

1-(4-Methylanilino)-4-(4-pyridyl methyl)phthalazine;

1-(3-Chloro-4-fluoroanilino)-4-(4-pyridylmethyl) phthalazine; and 1-(3-Methylanilino)-4-(4-pyridylmethyl)phthalazine.

A compound of the invention may be prepared by processes known perse for example as described in the working examples infra.

Pharmaceutical Preparations, Methods, and Uses

The present invention relates also to pharmaceutical compositions that comprise a compound of formula I (or an N-oxide thereof) as active ingredient and that can be used especially in the treatment of the diseases mentioned at the beginning. Compositions for enteral administration, such as nasal, buccal, rectal, topical ocular or, especially, oral administration, and for parenteral administration, such as intravenous, intramuscular, intravitreal, sub-conjunctival or subcutaneous administration, to warm-blooded animals, especially humans, are especially preferred. The compositions comprise the active ingredient alone or, preferably, together with a pharmaceutically acceptable carrier. The dosage of the active ingredient depends upon the disease to be treated and upon the species, its age, weight, and individual condition, the individual pharmacokinetic data, and the mode of administration.

The pharmaceutical compositions comprise from approximately 1% to approximately 95% active ingredient, single-dose administration forms comprising in the preferred embodiment from approximately 20% to approximately 90% active ingredient and forms that are not of single-dose type comprising in the preferred embodiment from approximately 5% to approximately 20% active ingredient. Unit dose forms are, for example, coated and uncoated tablets, ampoules, vials, suppositories, or capsules. Further dosage forms are, for example, injectables, intraocular devices, intravitreal devices, ointments, creams, pastes, foams, tinctures, lip-sticks, drops, sprays, dispersions, etc. Examples are capsules containing from about 0.05 g to about 1.0 g active ingredient.

The pharmaceutical compositions of the present invention are prepared in a manner known per se, for example by means of conventional mixing, granulating, coating, dissolving or lyophilizing processes.

Preference is given to the use of solutions of the active ingredient, and also suspensions or dispersions, especially isotonic aqueous solutions, dispersions or suspensions which, for example in the case of lyophilized compositions comprising the active ingredient alone or together with a carrier, for example mannitol, can be made up before use. The pharmaceutical compositions may be sterilized and/or may comprise excipients, for example preservatives, stabilizers, wetting agents and/or emulsifiers, solubilizers, salts for regulating osmotic pressure and/or buffers and are prepared in a manner known per se, for example by means of conventional dissolving and lyophilizing processes. The said solutions or suspensions may comprise viscosity-increasing agents, typically sodium carboxymethylcellulose, carboxymethylcellulose, dextran, polyvinylpyrrolidone, or gelatins, or also solubilizers, for example Tween 80[polyoxyethylene(20)sorbitan mono-oleate; trademark of ICI Americas, Inc, USA].

Suitable carriers are especially fillers, such as sugars, for example lactose, saccharose, mannitol or sorbitol, cellulose preparations, and/or calcium phosphates, for example tricalcium phosphate or calcium hydrogen phosphate, and also binders, such as starches, for example corn, wheat, rice or potato starch, methylcellulose, hydroxypropyl methylcellulose, sodium carboxymethylcellulose, and/or polyvinylpyrrolidone, and/or, if desired, disintegrators, such as the above-mentioned starches, also carboxymethyl starch, crosslinked polyvinylpyrrolidone, alginic acid or a salt thereof, such as sodium alginate. Additional excipients are especially flow conditioners and lubricants, for example silicic acid, talc, stearic acid or salts thereof, such as magnesium or calcium stearate, and/or polyethylene glycol, or derivatives thereof.

Pharmaceutical compositions for oral administration also include hard capsules containing gelatin, and also soft, sealed capsules consisting of gelatin and a plasticizer, such as glycerol or sorbitol. The hard capsules may contain the active ingredient in the form of granules, for example in admixture with fillers, such as corn starch, binders, and/or glidants, such as talc or magnesium stearate, and optionally stabilizers. In soft capsules, the active ingredient is preferably dissolved or suspended in suitable liquid excipients, such as fatty oils, paraffin oil or liquid polyethylene glycols or fatty acid esters of ethylene or propylene glycol, to which stabilizers and detergents, for example of the polyoxyethylene sorbitan fatty acid ester type, may also be added.

The invention relates likewise to a process or a method for the treatment of one of the pathological conditions mentioned hereinabove, especially ischemic retinopathy, retinal neovascularization and choroidal neovascularization. The compounds of formula I (or an N-oxide thereof) can be administered as such or especially in the form of pharmaceutical compositions, prophylactically or therapeutically, preferably in an amount effective against the said diseases, to a warm-blooded animal, for example a human, requiring such treatment. In the case of an individual having a bodyweight of about 70 kg the daily systemic dose administered is from approximately 0.1 g to approximately 5 g, preferably from approximately 0.5 g to approximately 2 g, of a compound of the present invention.

The present invention relates especially also to the use of a compound of formula I (or an N-oxide thereof), or a pharmaceutically acceptable salt thereof, especially a compound of formula I which is said to be preferred, or a pharmaceutically acceptable salt thereof, as such or in the form of a pharmaceutical formulation with at least one pharmaceutically acceptable carrier for the therapeutic and also prophylactic management of one or more of the diseases mentioned hereinabove, especially ischemic retinopathy, retinal neovascularization and choroidal neovascularization.

The present invention relates especially also to the use of a compound of formula I (or an N-oxide thereof), or a pharmaceutically acceptable salt thereof, especially a compound of formula I which is said to be preferred, or a pharmaceutically acceptable salt thereof, as such or in the form of a pharmaceutical formulation with at least one pharmaceutically acceptable carrier for the therapeutic and also prophylactic management of one or more of the diseases mentioned hereinabove, especially ischemic retinopathy, retinal neovascularization and choroidal neovascularization.

The present invention relates especially also to the use of a compound of formula I (or an N-oxide thereof), or a pharmaceutically acceptable salt thereof, especially a compound of formula I which is said to be preferred, or a pharmaceutically acceptable salt thereof, for the preparation of a pharmaceutical formulation for the therapeutic and also prophylactic management of one or more of the diseases mentioned hereinabove, especially ischemic retinopathy, retinal neovascularization and choroidal neovascularization.

The preferred dose quantity, composition, and preparation of pharmaceutical formulations (medicines) which are to be used in each case are described above.

The following Examples serve to illustrate the invention without limiting the invention in its scope.

Temperatures are measured in degrees celsius. Unless otherwise indicated, the reactions take place at room temperature.

The short forms and abbreviations used have the following definitions:

| | |
|---|---|
| DMSO | dimethyl sulfoxide |
| ESI-MS | electrospray ionization mass spectroscopy |
| Ether | diethyl ether |
| h | hour(s) |

| | |
|---|---|
| HV | high vacuum |
| RE | rotary evaporator |
| RT | room temperature |
| m.p. | melting point |
| THF | tetrahydrofuran |

EXAMPLE 1

1-(4-Chloroanilino)-4-(4-pyridylmethyl)phthalazine Dihydrochloride

A mixture of 15.22 g (59.52 mmol) 1-chloro-4-(4-pyridylmethyl)phthalazine (for preparation see German Auslegeschrift no. 1 061 788 [published Jul. 23, 1959]), 7.73 g (60.59 mmol) 4-chloroaniline and 200 ml 1-butanol is heated for 2 h under reflux. The crystallizate which is obtained when the mixture slowly cools to 5° C. is then filtered off and washed with 1-butanol and ether. The filter residue is dissolved in about 200 ml hot methanol, the solution is treated with 0.75 g activated carbon and filtered via a Hyflo Super Cel, and the pH of the filtrate is adjusted to about 2.5 with 7 ml 3N methanolic HCl. The filtrate is evaporated to about half the original volume and ether added until slight turbidity occurs; cooling then leads to the precipitation of crystals. The crystallizate is filtered off, washed with a mixture of methanol / ether (1:2) as well as ether, dried for 8 h at 110° C. under HV, and equilibrated for 72 h at 20° C. and in room atmosphere. In this way, the title compound is obtained with a water content of 8.6%; m.p. >270° C.; $^1$H NMR (DMSO-$d_6$) 11.05–12.20 (br), 9.18–9.23 (m, 1H), 8.88 (d, 2H), 8.35–8.40 (m, 1H), 8.18–8.29 (m, 2H), 8.02 (d, 2H), 7.73 (d, 2H), 7.61 (d, 2H), 5.02 (s, 2H); ESI-MS: (M+H$^+$=347.

EXAMPLE 2

1-(4-Chloroanilino)-4-(4-pyridylmethyl)phthalazine Hydrochloride (Formula:  ·HCl)

A mixture of 0.972 g (3.8 mmol) 1-chloro-4-(4-pyridylmethyl)phthalazine, 0.656 g (4 mmol) 4-chloroaniline hydrochloride (Research Organics, Inc., Cleveland, Ohio, USA) and 20 ml ethanol is heated for 2 h under reflux. The reaction mixture is cooled in an ice bath, filtered, and the crystallizate washed with a little ethanol and ether. After drying under HV for 8 h at 110° C. and for 10 h at 150° C., the title compound is obtained as a result of thermal removal of HCl; m.p. >270° C.; $^1$H NMR (DMSO-$d_6$) 9.80–11.40 (br), 8.89–8.94 (m, 1H), 8.67 (d, 2H), 8.25–8.30 (m, 1H), 8.06–8.17 (m, 2H), 7.87 (d, 2H), 7.69 (d, 2H), 7.49 (d, 2H), 4.81 (s, 2H); ESI-MS: (M+H)$^+$=347.

EXAMPLE 3

1-(4-Chloroanilino)-4-(4-pyridylmethyl)phthalazine Hydrochloride

A mixture of 1.28 g (5 mmol) 1-chloro-4-(4-pyridylmethyl)phthalazine, 0.67 g (5.25 mmol) 4-chloroaniline and 15 ml 1-butanol is heated for 0.5 h at 100 h while stirring in a nitrogen atmosphere. The mixture is then cooled to RT, filtered, and the filtrate washed with 1-butanol and ether. For purification, the crystallizate is dissolved in 40 ml of hot methanol, the solution treated with activated carbon, filtered via Hyflo Super Cel, and the filtrate evaporated to about half its original volume, resulting in the formation of a crystalline precipitate. After cooling to 0° C., filtration, washing of the filter residue with ether, and drying under HV for 8 h at 130° C., the title compound is obtained; m.p. >270° C.; 1H NMR (DMSO-$d_6$) 9.80–11.40 (br), 8.89–8.94 (m, 1H), 8.67 (d, 2H), 8.25–8.30 (m, 1H), 8.06–8.17 (m, 2H), 7.87 (d, 2H), 7.69 (d, 2H), 7.49 (d, 2H), 4.81 (s, 2H); ESI-MS: (M+H)$^+$=347.

EXAMPLE 4

1-(4-Chloroanilino)-4-(4-pyridylmethyl)phthalazine

A mixture of 14.19 g (0.1 mol) phosphorus pentoxide, 13.77 g (0.1 mol) triethylamine hydrochloride and 12.76 g (0.1 mol) 4-chloroaniline is heated and stirred in a nitrogen atmosphere at 200° C. until a homogeneous melt has formed (about 20 min). To the melt, 5.93 g (0.025 mol) 4-(4-pyridylmethyl)-1(2H)-phthalazinone (for preparation see German Auslegeschrift no. 1 061 788 [published 23.07.1959]) is added, and the reaction mixture is stirred for 3 h at 200° C. After the reaction mixture has cooled to about 100° C., 200 ml of water is added. Stirring is continued until the temperature reaches about 30° C., and then 20 ml conc. ammonia (30% aqueous ammonium hydroxide solution) and 900 ml chloroform are added consecutively. As soon as a diphasic mixture has formed, the organic phase is separated off, dried over anhydrous sodium sulfate, filtered, and the filtrate evaporated on a RE to a volume of about 50 ml, to which 100 ml acetate is then added, and the mixture is cooled in an ice bath. The crystallizate obtained is filtered off and washed with acetate and ether. After recrystallization from methanol and drying under HV for 8 h at 120° C., the title compound is obtained; m.p. 194–195° C.; ESI-MS: (M+H)$^+$=347.

What is claimed is:

1. A method of treating or preventing ocular neovascular diseases, comprising administering to a subject in need of such treatment an effective amount of a compound of formula I or a salt thereof, wherein formula I is (1)

wherein
n is 0 to 2,
R is H or lower alkyl;
X is imino, oxa, or thia;
Y is aryl; and
Z is unsubstituted or substituted pyridyl;
or an N-oxide of the defined compound, wherein 1 or more N atoms carry an oxygen atom.

2. The method of claim 1, wherein said neovascular diseases are choroidal and retinal neovascularization.

3. The method of claim 1, wherein said neovascular disease is exudative age related macular degeneration.

4. The method of claim 1, wherein said neovascular disease is proliferative diabetic retinopathy.

5. The method of claim 1, wherein said neovascular diseases are ischemic retinopathies.

6. The method of claim 1, wherein said subject is a human or a mammal.

7. The method of claim 1, wherein
n is 0 or 1,
R is H or lower alkyl,
X is imino, oxa, or thia,
Y is unsubstituted phenyl or phenyl substituted with one or two substituents independently selected from the group consisting of lower alkenyl, lower alkoxycarbonyl, lower alkylcarbamoyl, lower alkanoyl, phenyloxy, halogen-lower alkyloxy, lower alkoxycarbonyl, lower alkylmercapto, halogen-lower alkylsulfonyl, dihydroxybora (—B(OH)$_2$)), 2-methyl pyrimidyin-4-yl, oxazol-5-yl, 2-methyl- 1,3-dioxolan-2-yl, 1h-pyrazol-3-yl, 1-methyl-pyrazol-3-yl, lower alkylenedioxy bound to two adjacent C-atoms, pyridyl, 4-chloro-2-fluoroanilino, amino, lower alkanoylamino, halogen, lower alkyl, halogen-lower alkyl, hydroxy, lower alkoxy, phenyl-lower alkoxy, and cyano; and
Z is 3- or 4-pyridyl, lower alkyl, halogen-lower alkyl, lower alkoxy or hydroxy, wherein said pyridyl is unsubstituted or is substituted by one or two substituents independently of one another from the group comprising halogen.

8. The method of claim 1, wherein
n is 0 or 1,
R is H,
X is imino,
Y is unsubstituted phenyl or phenyl substituted with one or two substituents independently selected from the group consisting of lower alkanoylamino, halogen, lower alkyl, halogen-lower alkyl, hydroxy, lower alkoxy, phenyl-lower alkoxy, cyano, and amino, and
Z is selected from the group consisting of 4-pyridyl, lower alkyl, halogen-lower alkyl, hydroxy and lower alkoxy, wherein pyridyl is unsubstituted or is substituted by halogen.

9. The method of claim 1, wherein
n is 0 or 1,
R is H,
X is imino,
Y is unsubstituted phenyl or phenyl substituted with one or two substituents independently selected from the group consisting of lower alkyl, halogen-lower alkyl, hydroxy, lower alkoxy cyano and halogen, and
Z is 4-pyridyl, lower alkyl, halogen-lower alkyl, hydroxy, or lower alkoxy, wherein said pyridyl is substituted or unsubstituted by a halogen.

10. The method of claim 1, wherein
n is 0,
X is imino,
Y is unsubstituted phenyl or phenyl substituted with one or two substituents independently selected from the group consisting of methyl, trifluoromethyl, hydroxy, cyano, methoxy, fluorine, and chlorine, and
Z is 4-pyridyl, methyl, trifluoromethyl, hydroxy or methoxy, wherein said pyridyl is substituted or unsubstituted by fluorine or chlorine.

11. The method of claim 1, wherein
n is 0,
X is imino,
Y is unsubstituted phenyl or phenyl substituted with one or two substituents independently selected from the group consisting of methyl, methoxy, cyano, trifluoromethyl, chlorine, and fluorine, and
Z is 4-pyridyl or methyl, wherein said pyridyl is substituted or unsubstituted by chlorine or fluorine.

12. The method of claim 1, wherein said compound is selected from the group consisting of:
1-(4-Methylanilino)-4-(4-pyridylmethyl)phthalazine;
1-(3-Chloroanilino)-4-(4-pyridylmethyl)phthalazine;
1-Anilino-4-(4-pyridylmethyl)phthalazine;
1-Benzylamino-4-(4-pyridylmethyl)phthalazine;
1-(4-Methoxyanilino)-4-(4-pyridylmethyl)phthalazine;
1-(3-Benzyloxyanilino)-4-(4-pyridylmethyl)phthalazine;
1-(3-Methoxyanilino)-4-(4-pyridylmethyl)phthalazine;
1-(2-Methoxyanilino)-4-(4-pyridylmethyl)phthalazine;
1-(4-Trifluoromethylanilino)-4-(4-pyridylmethyl) phthalazine;
1-(4-Fluoroanilino)-4-(4-pyridylmethyl)phthalazine;
1-(3-Hydroxyanilino)-4-(4-pyridylmethyl)phthalazine;
1-(4-Hydroxyanilino)-4-(4-pyridylmethyl)phthalazine;
1-(3-Aminoanilino)-4-(4-pyridylmethyl)phthalazine;
1-(3,4-Dichloroanilino)-4-(4-pyridylmethyl)phthalazine;
1-(4-Bromoanilino)-4-(4-pyridylmethyl)phthalazine;
1-(3-Chloro-4-methoxyanilino)-4-(4-pyridylmethyl) phthalazine;
1-(4-Cyanoanilino)-4-(4-pyridylmethyl)phthalazine;
1-(3-Chloro-4-fluoroanilino)-4-(4-pyridylmethyl) phthalazine;
1-(3-Methylanilino)-4-(4-pyridylmethyl)phthalazine; and
pharmaceutically acceptable salts thereof.

13. The method of claim 1, wherein said compound is 1-(3-Chloroanilino)-4-(4-pyridylmethyl)phthalazine and said method treats human ocular neovascular diseases.

* * * * *

UNITED STATES PATENT AND TRADEMARK OFFICE
CERTIFICATE OF CORRECTION

PATENT NO.    : 6,271,233 B1
DATED         : August 7, 2001
INVENTOR(S)   : Brazzell et al.

It is certified that error appears in the above-identified patent and that said Letters Patent is hereby corrected as shown below:

<u>Title page,</u>
Item [73], Assignee change "CIBA Vision Corporation, Deluth, GA (US)" to
-- Novartis AG, Basel (CH) --.
OTHER PUBLICATIONS, in the third reference change "compliclations" to
-- complications --.

Signed and Sealed this

Third Day of September, 2002

*Attest:*

JAMES E. ROGAN
*Attesting Officer*    *Director of the United States Patent and Trademark Office*